Figure 1:
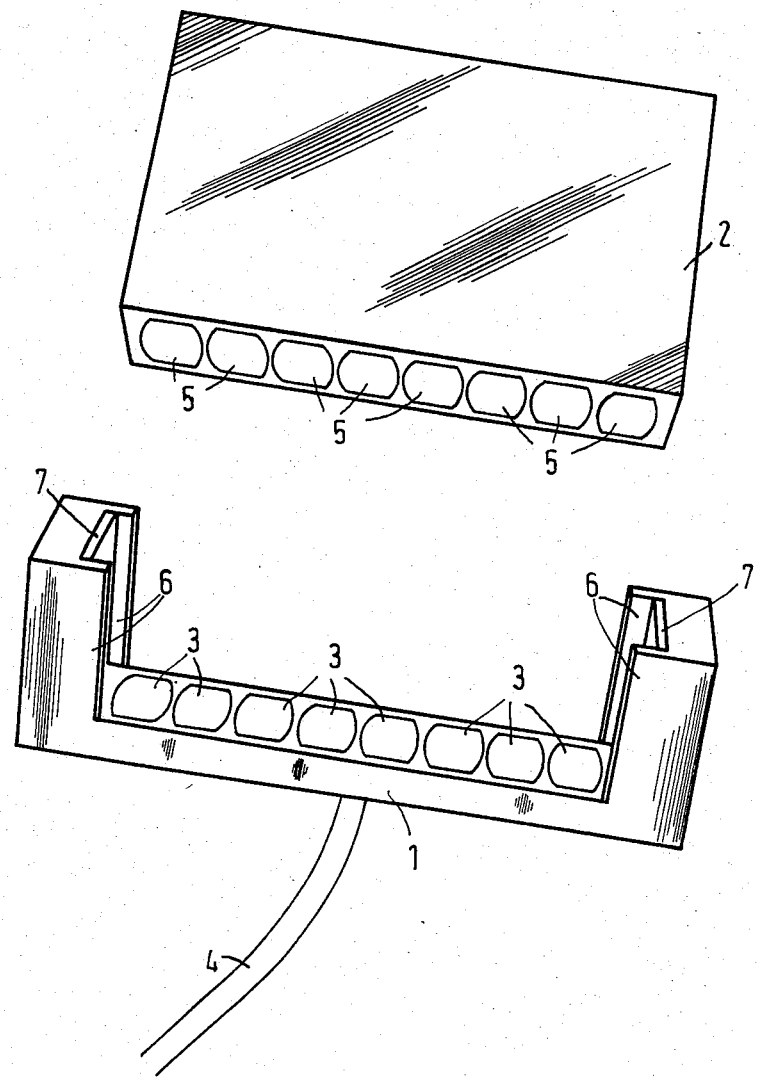

United States Patent [19]

Fischer et al.

[11] Patent Number: 4,509,815

[45] Date of Patent: Apr. 9, 1985

[54] TEST HEAD MOUNTING FOR SINGLE OR MULTIPLE TEST HEADS

[75] Inventors: Gert Fischer, Mulheim; Dieter Lather, Geldern, both of Fed. Rep. of Germany

[73] Assignee: Mannesmann Aktiengesellschaft, Fed. Rep. of Germany

[21] Appl. No.: 378,117

[22] Filed: May 14, 1982

[30] Foreign Application Priority Data

May 29, 1981 [DE] Fed. Rep. of Germany ....... 3122036

[51] Int. Cl.³ .............................................. H01R 3/00
[52] U.S. Cl. ............................ 339/147 P; 174/70 R; 339/65; 361/283
[58] Field of Search ................. 339/65, 147 R, 147 P; 361/271, 283, 326, 328, 329; 174/70 R

[56] References Cited

U.S. PATENT DOCUMENTS

| 1,667,885 | 5/1928 | De Mott et al. | 361/326 |
| 3,264,601 | 8/1966 | Hartholz | 339/65 X |
| 3,649,742 | 3/1972 | Tissot | 174/70 R |
| 4,118,090 | 10/1978 | Del Mei | 339/65 X |
| 4,310,906 | 1/1982 | Cantrell, Jr. et al. | 361/283 X |

FOREIGN PATENT DOCUMENTS 316104 11/1919 Fed. Rep. of Germany ...... 361/329

Primary Examiner—Z. R. Bilinsky
Attorney, Agent, or Firm—Oldham, Oldham & Weber Co.

[57] ABSTRACT

The invention relates to a test head mounting for single or multiple test heads in ultrasonic testing in immersion technique process. To reduce expenditure in the replacement of the test heads, a capacitive coupling is proposed between the test head and mounting element for the test head.

1 Claim, 1 Drawing Figure

TEST HEAD MOUNTING FOR SINGLE OR MULTIPLE TEST HEADS

The invention relates to a test head mounting for single or multiple test heads in ultrasonic testing.

In single or multiple test heads known to date, the active oscillator elements have fixed cable connections with varied cable lengths.

The replacement of the single or multiple oscillators in the known forms of embodiment is in many cases of application only possible with a considerable expenditure of time. According to the construction of the test head mountings currently in use it is a disadvantage that a readjustment of the mechanical test head setting becomes necessary.

The object of the invention is to create a test head mounting for single or multiple test heads, which in separated construction makes a readjustment unnecessary, and as a result of the extensive possibilities of application eliminates the disadvantages occurring to date and makes replacement possible in a substantially shorter time and with reduced expenditure.

To solve this problem, according to the invention, a test head mounting for single and multiple test heads is proposed.

With the embodiment, according to the invention, of a separated single or multiple test head, considerable advantages are achieved, owing to the capacitive coupling, compared with the rigid test heads known to date and with the coupling technology which is usual today.

In the attached drawing, a possible form of embodiment is represented diagrammatically for a test head mounting according to the invention.

In the form of embodiment of a multiple test head, illustrated in the drawing in perspective representation, the adaptive test head 2 has, for example, eight active oscillator elements, which are electrically connected with the condenser plates 5 firmly inserted in the base of the adaptive test head 2. The mounting element 1 has correspondingly associated condenser plates 3, which are likewise firmly inserted. To receive the adaptive test head 2, the mounting element 1 has the guide rails 6 and the stop element 7. The connection lead 4 serves as connection to the ultrasonic testing electronic equipment and in the prior art, would have been directly connected to the various oscillator elements.

Other arrangements of the condenser plates 3 and 5, for example in the form of a plug connection, are also conceivable.

The transmission of the high-frequency signals necessary for ultrasonic testing takes place directly on the test head through capacitive coupling. When defects occur on the active oscillator elements, therefore, only the adaptive test head 2 needs to be replaced. With corresponding accuracy in size of the guide rails 6 and the stop elements 7, a readjustment of the mechanical test head setting is no longer necessary.

What is claimed is:
1. A mounting assembly for test heads, comprising:
   a holding element;
   a replaceable test head adapted for receipt by said holding element;
   condenser plates firmly fixed in said holding element;
   condenser plates in said test head and having the same arrangement as those on the holding element when inserted into said holding element; and
   stop elements in said holding element for setting a space between said condenser plates on said holding element and said condenser plates on said test head and thereby defining a dielectrical distance.

* * * * *